United States Patent
Miller et al.

(10) Patent No.: US 8,029,528 B2
(45) Date of Patent: Oct. 4, 2011

(54) INSTRUMENT GUIDE AND METHOD FOR USE

(75) Inventors: Kenneth Lance Miller, Hamilton, OH (US); Salvatore Privitera, Mason, OH (US); James David Hughett, Sr., Liberty Township, OH (US)

(73) Assignee: AtriCure, Inc., West Chester, OH (US)

( * ) Notice: Subject to any disclaimer, the term of this patent is extended or adjusted under 35 U.S.C. 154(b) by 1476 days.

(21) Appl. No.: 11/254,057

(22) Filed: Oct. 19, 2005

(65) Prior Publication Data

US 2006/0167478 A1 Jul. 27, 2006

Related U.S. Application Data

(63) Continuation-in-part of application No. 11/028,901, filed on Jan. 3, 2005, now abandoned.

(51) Int. Cl.
*A61B 17/00* (2006.01)
*A61B 18/12* (2006.01)
(52) U.S. Cl. .......................... 606/190; 606/41
(58) Field of Classification Search ............ 606/41, 606/50–52, 108, 151–156, 190, 148, 213; 600/29, 30, 37, 585; 623/23.72; 604/174, 604/175, 179; 128/898
See application file for complete search history.

(56) References Cited

U.S. PATENT DOCUMENTS

| | | | |
|---|---|---|---|
| 2,134,152 A | 10/1938 | Schwarzmayr | |
| 3,104,077 A | 9/1963 | Struble | |
| 3,207,421 A | 9/1965 | Hunger et al. | |
| 3,308,940 A | 3/1967 | Morris, Jr. | |
| 3,460,742 A | 8/1969 | Langdon | |
| 4,887,615 A | 12/1989 | Taylor | |
| 5,033,477 A * | 7/1991 | Chin et al. | |
| 5,071,428 A * | 12/1991 | Chin et al. | |
| 5,125,928 A * | 6/1992 | Parins et al. | |
| 5,165,425 A * | 11/1992 | Vermot | 128/898 |
| 5,176,692 A | 1/1993 | Wilk | |
| 5,456,720 A | 10/1995 | Schultz | |
| 5,487,385 A * | 1/1996 | Avitall | |
| 5,500,012 A * | 3/1996 | Brucker et al. | |
| 5,575,766 A * | 11/1996 | Swartz et al. | |
| 5,593,441 A | 1/1997 | Lichtenstein et al. | |
| 5,687,896 A | 11/1997 | Clift | |
| 5,687,924 A | 11/1997 | Reiche et al. | |
| 5,718,666 A * | 2/1998 | Alarcon | 600/249 |
| 5,730,127 A * | 3/1998 | Avitall | |

(Continued)

FOREIGN PATENT DOCUMENTS

WO    WO 96/31155    10/1996

(Continued)

OTHER PUBLICATIONS

The Dow Chemical Company, *Typical Physical Properties of Pellethane*, 9 pages, Printed in U.S.A., Aug. 2001.

(Continued)

*Primary Examiner* — Kathleen Sonnett
(74) *Attorney, Agent, or Firm* — Cook Alex Ltd.

(57) ABSTRACT

An instrument guide and method for use. An elongate flexible body has a proximal end and a distal end. The elongate body has two portions, one or more resilient than the other. A distal pocket is positioned adjacent the distal end of the elongate flexible body. An anchor is provided to attach the guide to a surgical instrument.

5 Claims, 6 Drawing Sheets

U.S. PATENT DOCUMENTS

| | | | |
|---|---|---|---|
| 5,740,808 A * | 4/1998 | Panescu et al. | |
| 5,766,187 A * | 6/1998 | Sugarbaker | 606/148 |
| 5,785,706 A * | 7/1998 | Bednarek | |
| 5,814,028 A * | 9/1998 | Swartz et al. | |
| 5,842,984 A * | 12/1998 | Avitall | |
| 5,855,590 A * | 1/1999 | Malecki et al. | |
| 5,876,398 A * | 3/1999 | Mulier et al. | |
| 5,921,924 A * | 7/1999 | Avitall | |
| 5,922,026 A | 7/1999 | Chin | |
| 5,971,983 A * | 10/1999 | Lesh | |
| 6,010,531 A * | 1/2000 | Donlon et al. | |
| 6,012,457 A * | 1/2000 | Lesh | |
| 6,015,382 A * | 1/2000 | Zwart et al. | 600/207 |
| 6,024,740 A * | 2/2000 | Lesh et al. | |
| 6,036,670 A * | 3/2000 | Wijeratne et al. | |
| 6,047,218 A * | 4/2000 | Whayne et al. | |
| 6,071,281 A * | 6/2000 | Burnside et al. | |
| 6,080,168 A | 6/2000 | Levin | |
| 6,117,101 A * | 9/2000 | Diedrich et al. | |
| 6,123,703 A * | 9/2000 | Tu et al. | |
| 6,142,994 A * | 11/2000 | Swanson et al. | |
| 6,216,931 B1 | 4/2001 | Trawinski | |
| 6,224,543 B1 | 5/2001 | Gammons et al. | |
| 6,224,616 B1 | 5/2001 | Kugel | |
| 6,264,087 B1 | 7/2001 | Whitman | |
| 6,311,692 B1 * | 11/2001 | Vaska et al. | |
| 6,314,962 B1 * | 11/2001 | Vaska et al. | |
| 6,314,963 B1 * | 11/2001 | Vaska et al. | |
| 6,447,507 B1 * | 9/2002 | Bednarek et al. | |
| 6,474,340 B1 * | 11/2002 | Vaska et al. | |
| 6,936,052 B2 | 8/2005 | Gellman et al. | |
| 7,101,381 B2 | 9/2006 | Ford et al. | |
| 2002/0002329 A1 * | 1/2002 | Avitall | |
| 2002/0019629 A1 | 2/2002 | Dietz et al. | |
| 2002/0082595 A1 * | 6/2002 | Langberg et al. | |
| 2002/0099364 A1 * | 7/2002 | Lalonde | |
| 2002/0115990 A1 * | 8/2002 | Acker | |
| 2002/0120263 A1 * | 8/2002 | Brown et al. | |
| 2002/0156488 A1 | 10/2002 | Gellman et al. | |
| 2002/0183738 A1 * | 12/2002 | Chee et al. | |
| 2003/0028187 A1 * | 2/2003 | Vaska et al. | |
| 2003/0060822 A1 * | 3/2003 | Schaer et al. | |
| 2003/0069577 A1 * | 4/2003 | Vaska et al. | |
| 2003/0078574 A1 * | 4/2003 | Hall et al. | |
| 2003/0093104 A1 * | 5/2003 | Bonner et al. | |
| 2003/0125726 A1 * | 7/2003 | Maguire et al. | |
| 2003/0125729 A1 * | 7/2003 | Hooven et al. | 606/41 |
| 2003/0130598 A1 * | 7/2003 | Manning et al. | |
| 2003/0135207 A1 * | 7/2003 | Langberg et al. | |
| 2003/0144657 A1 * | 7/2003 | Bowe et al. | |
| 2003/0149440 A1 | 8/2003 | Kammerer et al. | |
| 2003/0176762 A1 | 9/2003 | Kammerer | |
| 2004/0216748 A1 | 11/2004 | Chin | |
| 2004/0249368 A1 | 12/2004 | Hooven | |
| 2006/0149121 A1 | 7/2006 | Hughett, Sr. et al. | |
| 2006/0167478 A1 | 7/2006 | Miller et al. | |

FOREIGN PATENT DOCUMENTS

| | | |
|---|---|---|
| WO | WO 01/21231 A2 | 3/2001 |

OTHER PUBLICATIONS

Pellethane Thermoplastic Polyurethane Elastomers, Dow Engineering Plastics, www.dow.com/engineeringplastics/prod/na/pel.htm p. 1 and 2, Oct. 29, 2004.

Mehall et al., "Bilateral Vats Pulmonary Vein Isolation, Left Atrial Appendage . . . " CTSNet, www.ctsnet.org/sections/clinicalresources/adultcardiac/expert_tech-22.html, Mar. 16, 2007.

Office Action dated May 16, 2007, issued in U.S. Appl. No. 11/028,901.

Balkhy, et al., Minimally invasive atrial fibrillation ablation combined with a new technique for thoracoscopic stapling of the left atrial appendage: case report, Heart Surgery Forum, vol. 7(6), 2004, pp. 353-355.

* cited by examiner

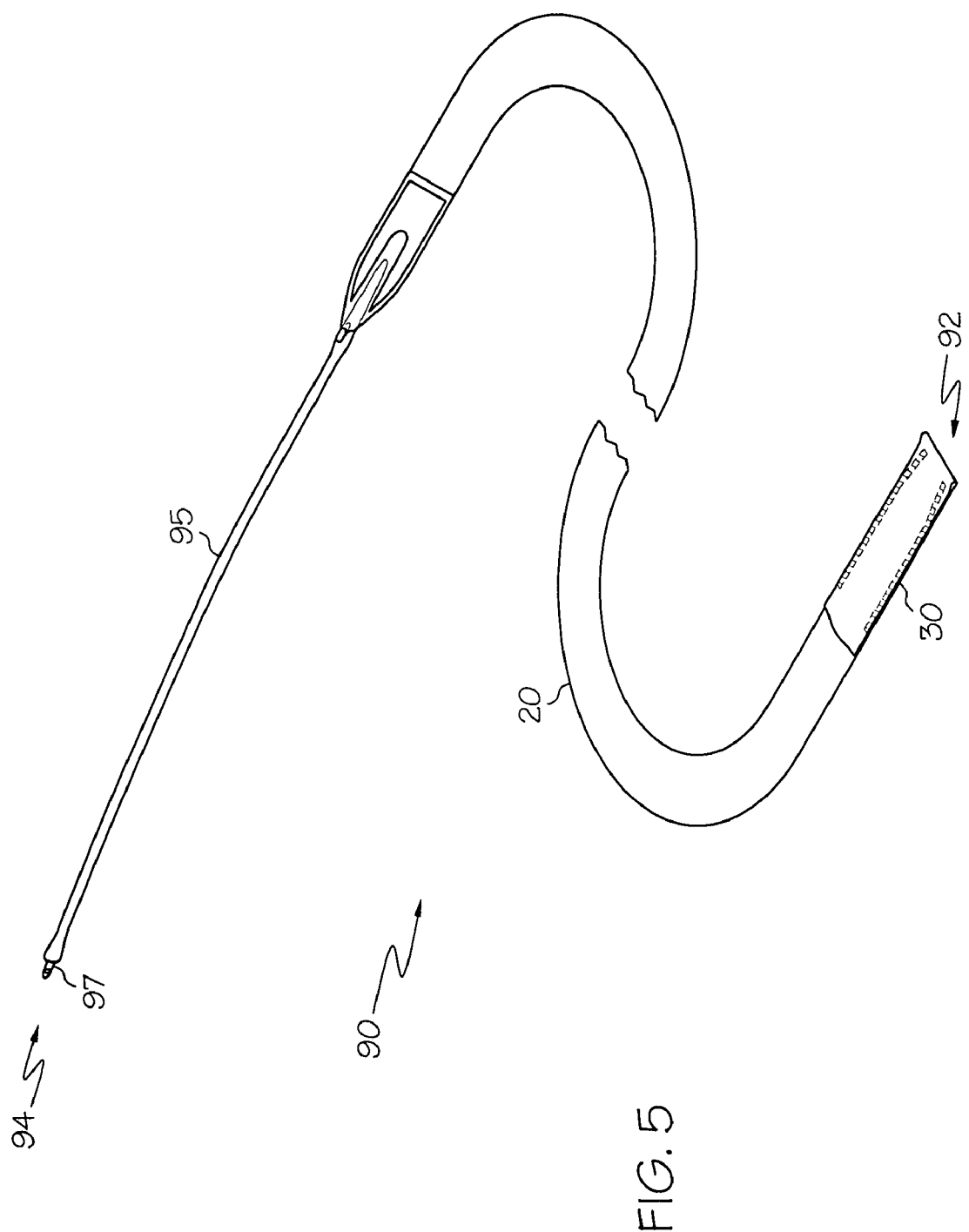

INSTRUMENT GUIDE AND METHOD FOR USE

RELATED APPLICATIONS

This is a continuation-in-part of application Ser. No. 11/028,901 filed on Jan. 3, 2005, now abandoned.

BACKGROUND

The present invention relates to surgical instruments, with one embodiment relating to guides for surgical instruments. Surgery generally refers to the diagnosis or treatment of injury, deformity, or disease. Most surgical procedures involve the use of one or more surgical instruments. In most cases, the surgical instrument must be positioned on or near target tissue of the patient. Target tissue refers to the desired destination, whether final or intermediate, of a surgical instrument, and may or may not include the tissue that is the subject of surgery. A variety of factors may make the placement of the surgical instrument challenging. For example, the shape, position, or sensitivity of the target tissue or surrounding anatomy may complicate positioning of a surgical instrument. As a further example, the geometry of the surgical instrument may pose complications in positioning the instrument. In yet another example, the nature or timing of the procedure may complicate placement of the surgical procedure. Another example is the size of the surgical field. Still other examples of circumstances may complicate positioning of surgical instruments. Instrument guides are sometimes used to facilitate placement of surgical instruments. No one, however, has previously made or used an instrument guide in accordance with the present invention.

BRIEF DESCRIPTION OF DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 illustrates another example of an instrument guide; and

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
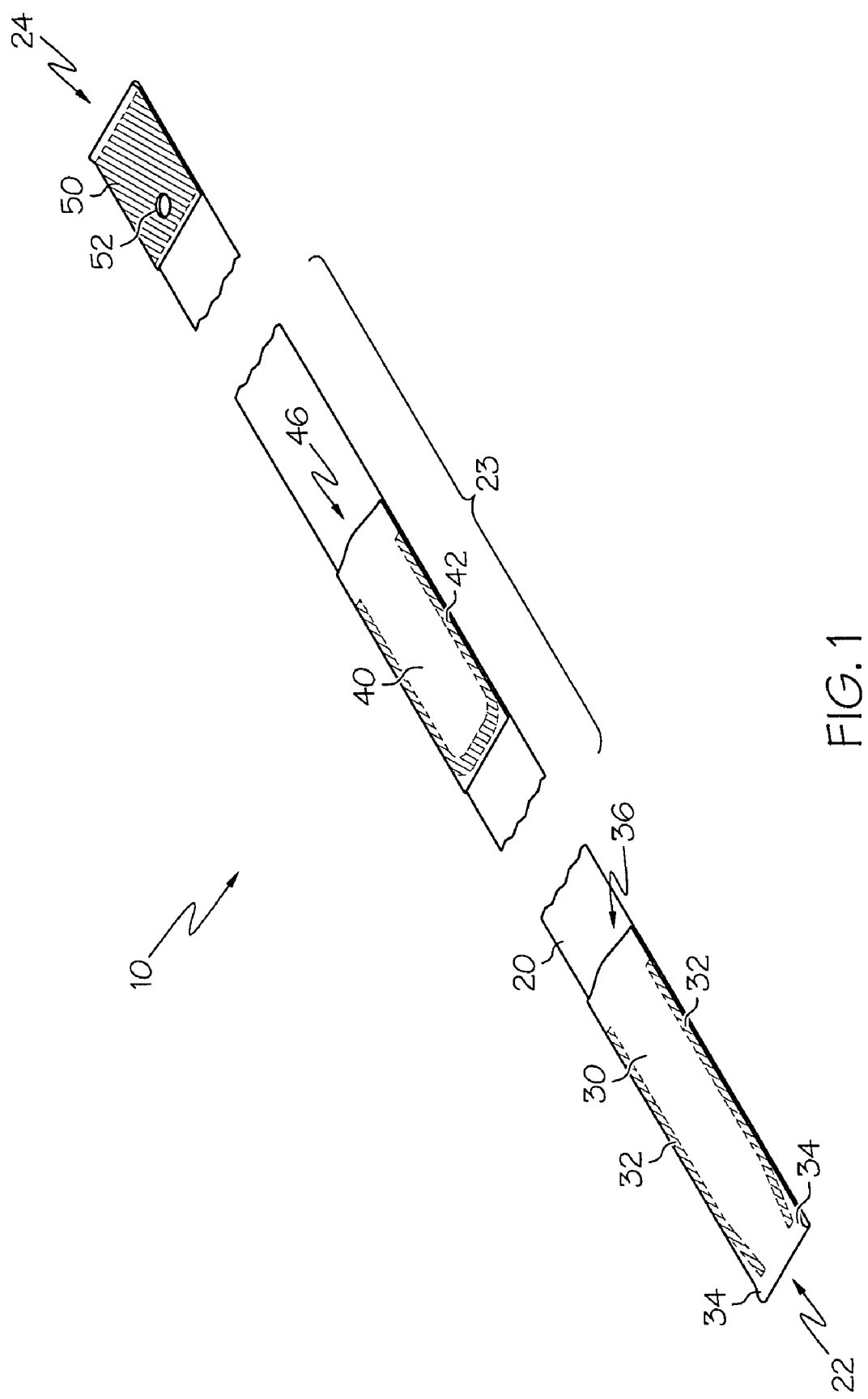
FIG. 1 illustrates an oblique view of an instrument guide.

FIG. 1 illustrates an example of an instrument guide (10). The instrument guide (10) includes an elongate flexible strip (20) having a distal end (22), a proximal end (24), and a medial portion (23) between the proximal and distal ends. Optionally, the elongate flexible strip (20) is formed at least in part of an elastomer. One suitable material is a polyurethane, such as PELETHANE series 2363 by DOW PLASTICS, but other materials may also be used. In the present embodiment, the elongate flexible strip (20) is in the form of a ribbon; however, other geometries could also be employed. The dimensions of the elongate flexible strip (20) may vary substantially, and in this example the ratio of width to length is about 0.01 to about 0.03. In the present embodiment, the elongate flexible strip (20) is about 30 to about 40 inches long, about 0.4 to about 0.8 inches wide, and about 0.001 to about 0.005 inches thick. For example, one embodiment has a nominal length of about 36 inches, a nominal width of about 0.75 inches, and a nominal thickness of about 0.003 inches.

A first pocket (30) is positioned adjacent the distal end (22) of the elongate flexible strip (20). As shown here, the distal pocket (30) has an opening (36) on the proximal end of the pocket, and the distal end of the pocket is substantially closed. The distal pocket (30) is formed by folding the elongate flexible strip (20) onto itself and adhering the walls to form seals (32). Heat or RF sealing or use of an adhesive are two exemplary techniques to adhere the walls. As shown here, the seals (32) tapered toward the distal end of the pocket. Two tabs (34) are provided at the distal end (22). Optionally, at least a portion of the distal pocket (30) is translucent or transparent.

The present embodiment has a second pocket (40) positioned proximally to the distal pocket (30) on the elongate flexible strip (20). As shown here, the second pocket (40) is positioned on the medial portion (23) of the elongate flexible strip (20). In this embodiment, the medial pocket (40) has an opening (46) on the proximal end of the pocket, and the distal end of the pocket is completely closed. The medial pocket (40) is formed by placing a section of material over the elongate flexible strip (20), preferably but not necessarily the same material, and adhering the walls to form the seal (42). As shown in this example, the distance from the distal end (22) of the elongate flexible strip (10) to the distal end of the medial pocket (40) is between about 15 inches to about 30 inches. In one embodiment, the nominal distance is about 21 inches.

An anchor (50) is positioned adjacent the proximal end (24) of the elongate flexible strip (20). The anchor (50) of the present embodiment includes a hole or eyelet (52), but other attachment mechanisms may be employed, such as holes, slits, hooks, fasteners, etc. Further, the anchor may have more than one anchor position. As shown here, the anchor (50) is formed by folding the elongate flexible strip (20) onto itself and adhering the walls together, such as with a heat seal or adhesive, thus increasing the wall thickness of the anchor (50). One advantage of increased wall thickness is to reinforce the eyelet (52). As shown in this example, the distance from the distal end of the medial pocket (40) to the eyelet (52) is between about 12 inches to about 13 inches. One embodiment has a nominal distance of about 12.5 inches.

One exemplary use of the instrument guide (10) is to deploy a surgical instrument. A positioning mechanism is placed in the distal pocket (30), and then by using the positioning mechanism the distal pocket (30) is advanced adjacent target tissue. The distal pocket (30) is preferably dimensioned to receive the positioning mechanism. The type positioning mechanism may vary widely, depending, for example, on the geometry of the target tissue and the surrounding anatomy. For instance, the positioning mechanism could be a surgeon's finger, a dissector, forceps, an articulated probe, and the like. The positioning mechanism may then be removed from the distal pocket (30). The tabs (34) may facilitate the removal of the positioning mechanism by providing a surface that the surgeon may grasp, such as with their fingers or with forceps, and pull the distal pocket (30) from the positioning mechanism.

The surgical instrument is placed in the medial pocket (40). The surgical instrument will vary depending upon the treatment and procedure being conducted in the surgery. The medial pocket (40) is preferably dimensioned to receive the appropriate surgical instrument. The elongate flexible strip (10) is then advanced further, such as by pulling the distal end (22) until the surgical instrument is adjacent the target tissue. The surgical instrument is removed from the medial pocket (40), such as by continuing to advance the elongate flexible strip (10) while keeping the surgical instrument stationary. Thus, the surgical instrument is successfully positioned adjacent the target tissue. The remainder of the elongate flexible strip (10) may then be removed from the surgical field. Optionally, the elongate flexible strip (10) may remain in the surgical field, before or after the surgical instrument is deployed, and function as a sling to hold or position tissue. Preferably, the portions of the instrument guide (10) that contact tissue in the surgical field may be free of sharp or abrasive edges.

Figure 2:
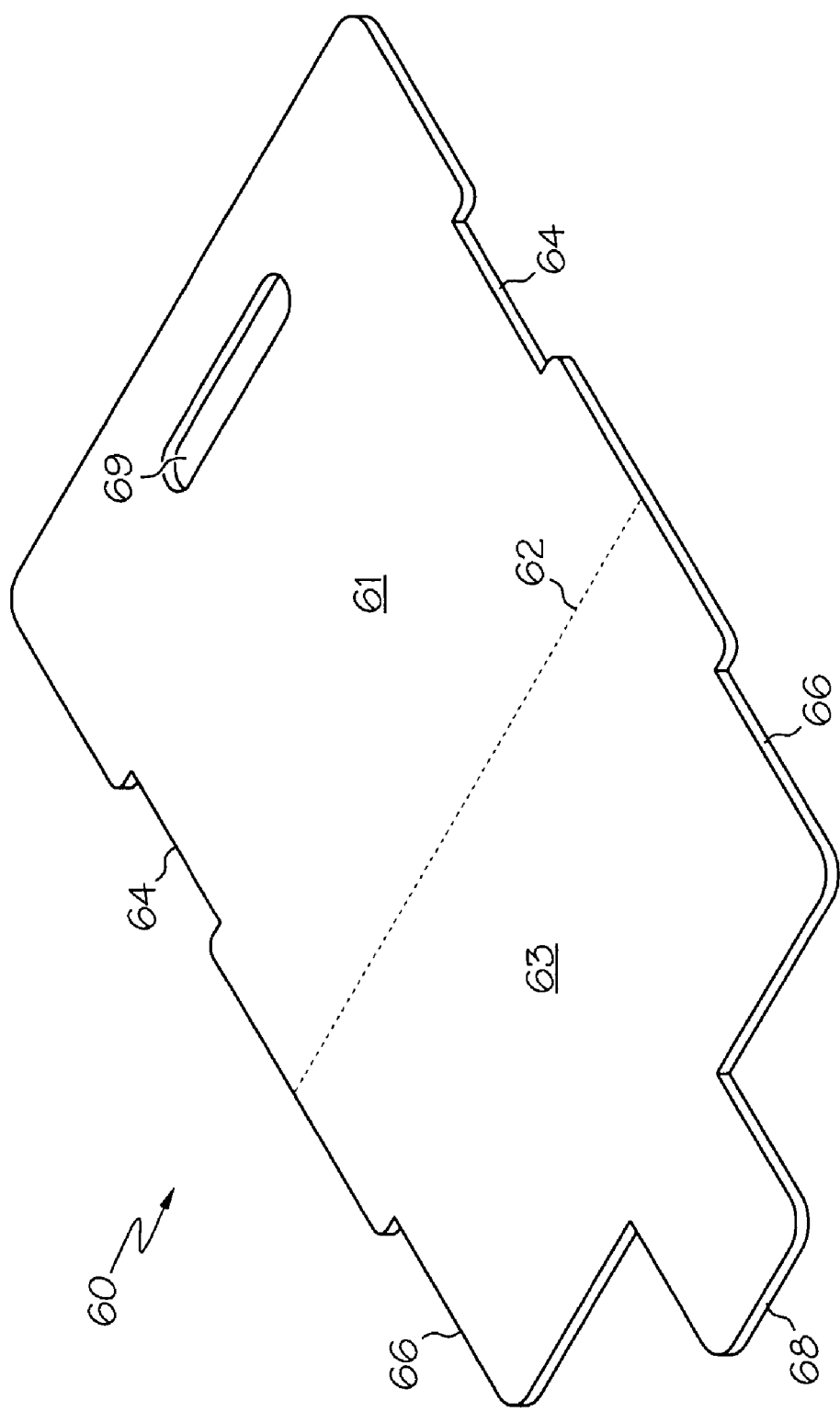
FIG. 2 illustrates an oblique view of a bobbin for holding an instrument guide.

FIG. 2 illustrates an optional bobbin (60) for holding the instrument guide (10). The bobbin (60) comprises a sheet of material foldable along a crease (62) that separates a base portion (61) and a cover portion (63). The bobbin (60) has an opened position (as shown in the figure) and a closed position where the cover portion (63) is folded onto the base portion (63). In the closed position, the recesses (64, 66) align with one another. The tab (68) mates with the slot (69) to function as a fastener to selectively hold the bobbin (60) in the closed position. Naturally, alternative fastening mechanisms may also be used. As shown in this embodiment, the bobbin (60) is made from a single sheet of material, such as 0.01 inch LEXAN 8040. The sheet has a nominal width of about 3 inches and a nominal length of about 5 inches.

In the opened position, the instrument guide (10) is wrapped between the recesses (64) starting the with proximal end (24). Before the entirety of the elongate flexible strip (20) is wrapped, the cover portion (63) is closed and fastened, and the remainder of the instrument guide (10) is wrapped between the recesses (66). The medial pocket (40) may be wrapped between recesses (64) in the opened position; however, the medial pocket could also be wrapped between recesses (66) in the closed position. The completely wrapped instrument guide (10) and bobbin (60) may then be stored in a sterilized and sealed pouch with instructions. Once the pouch opened, the surgeon unwraps a portion instrument guide (10) without releasing the tab (68). Thus, the surgeon may work with the distal pocket (30) and a portion of the elongate flexible strip (20) while the remainder of the instrument guide (10) is contained in the closed bobbin (60) and out of the way during the surgery. Once the surgeon is ready to advance the surgical instrument into the surgical field, the bobbin (60) may be opened and the remainder of the instrument guide (10) unwrapped and used. The bobbin (60) may then be discarded.

Figure 3:
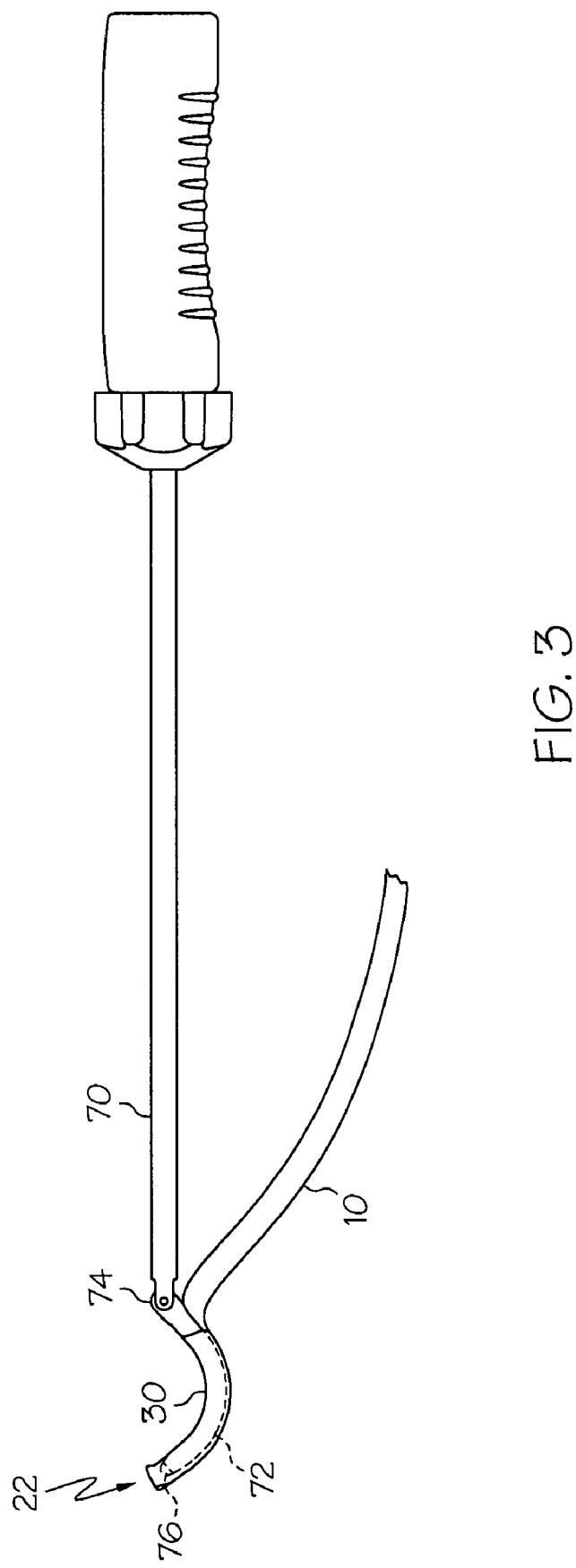
FIG. 3 illustrates an instrument guide with a positioning mechanism.
Figure 4:
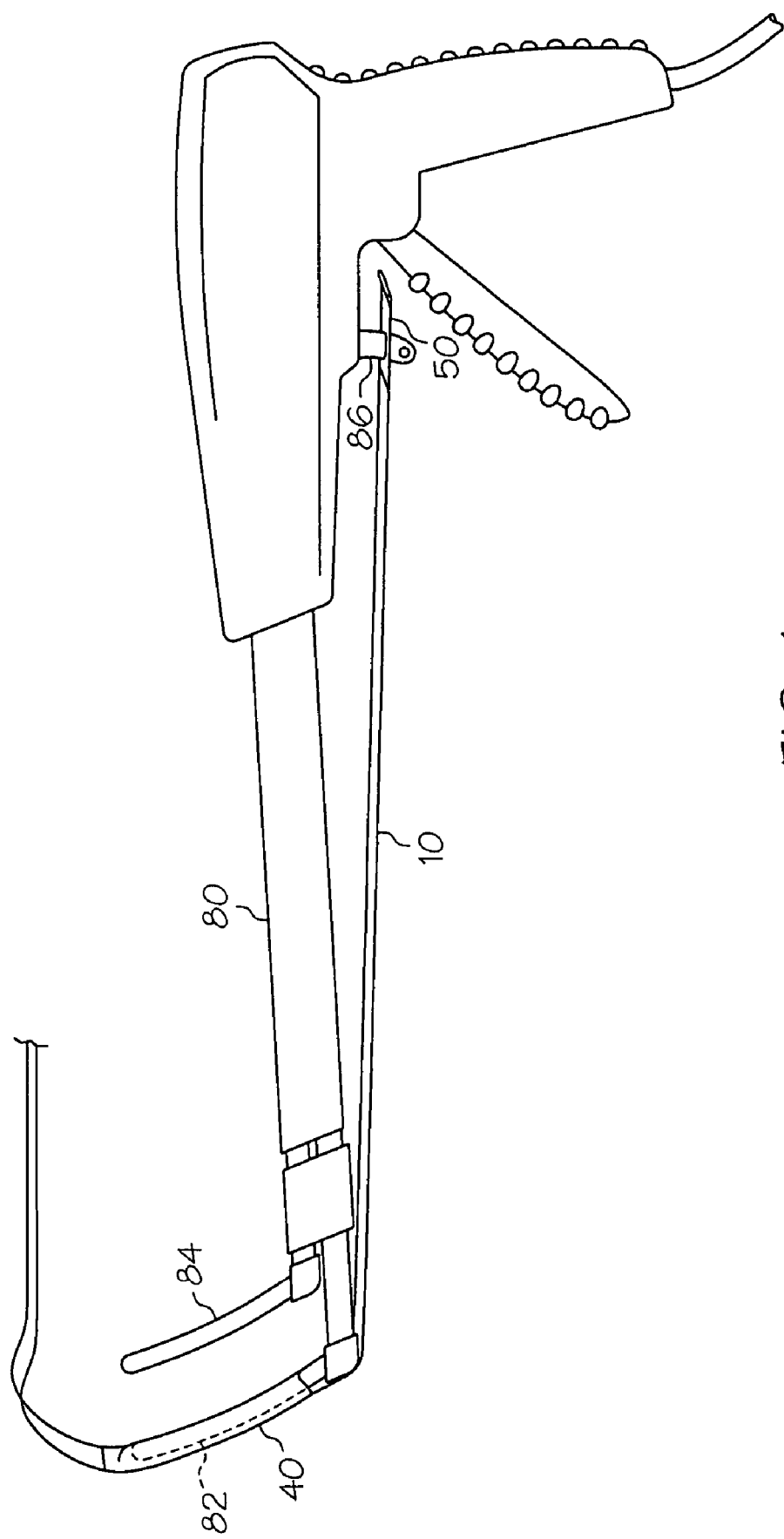
FIG. 4 illustrates an instrument guide attached to a surgical instrument.

FIGS. 3 and 4 illustrates an example of a procedure to use the instrument guide (10) in conjunction with a treatment for atrial fibrillation. It should be appreciated that numerous other surgical procedures, anatomies, and surgical instruments may be used, and the present example is merely an illustration of one embodiment of the invention. The positioning mechanism (70) in this example, shown here as a dissector, is placed in the distal pocket (30). The positioning mechanism (70) has an articulated shaft and includes an arcuate segment (72) that pivots about the joint (74). The arcuate segment (72) has blunt and rounded distal end (76). A light source emits visible energy from the distal end (76) that facilitates, among other things, locating the distal end (76) during a procedure and differentiating tissue. In this example, the distal pocket (30) is translucent.

The following describes an exemplary procedure using the positioning mechanism (70) to separate the left or right pair of pulmonary veins adjacent the left atrium. The procedure may be performed during open or minimally invasive surgery. With the arcuate segment (72) in the distal pocket (30), the distal end (76) of the arcuate segment (72) is positioned adjacent the junction of one of the pulmonary veins (superior or inferior) and the left atrium. The distal end (76) is advanced around the posterior of the pair of pulmonary veins while simultaneously pivoting the arcuate segment (72). The distal end (76) continues to advance until it emerges beyond the other adjacent pulmonary vein (the inferior or superior, as the case may be). The advancement of the distal end (76) separates the pair of pulmonary veins from the pericardial reflections, thus creating a dissected path between the pulmonary veins and the pericardium. The dissected path may be widened by sweeping the arcuate segment (72) and further separating the tissue and widening the dissected path. The surgeon may grasp the distal end (22) of the instrument guide (10) and pull the distal pocket (30) from the arcuate segment (72). The arcuate segment (72) may then be backed out and removed from the surgical field.

As illustrated in FIG. 4, the surgical instrument (80) in this example is a surgical clamp having a distal jaw (82) and a proximal jaw (84). In this example, the surgical instrument (80) is used to ablate tissue with RF energy (one example is disclosed in U.S. Pat. No. 6,517,536). One of the jaws, in this example the distal jaw (82), is placed in the medial pocket (40) of the instrument guide (10). The anchor (50) attaches to surgical instrument (80) to prevent the distal jaw (82) from inadvertently liberating from the medial pocket (40). As shown in this example, the anchor (50) attaches to the clamp release lever (86) and the instrument guide (10) remains taut between the anchor (50) and medial pocket (40). By continuing to pull the distal end (22) of the instrument guide (10), the distal jaw (82) may be accurately positioned in the dissected path until the pulmonary veins are interposed between the distal and proximal jaws (82, 84). The anchor (50) may then be detached. By pulling instrument guide (10), the medial pocket (40) may be pulled from the distal jaw (82). The instrument guide (10) may be removed from the surgical field. Alternatively, the instrument guide (10) can remain in the surgical field to hold or lift the vessels like a sling. The distal and proximal jaws (82, 84) may then be positioned such that the tissue being treated is interposed between the jaws. In one example, the tissue being treated is the atrium wall adjacent the pulmonary veins. The jaws may then be closed and the tissue ablated.

FIG. 5 illustrates another example of an instrument guide (90). The instrument guide (90) has an elongate flexible body with a distal end (92) and a proximal end (94). In the present example the body comprises two or more portions. While geometry or and materials in the portions can vary, as shown here the distal portion is an elongate flexible strip (20) similar to instrument guide (10), and the proximal portion is an elongate flexible member (95) having a generally round cross-sectional geometry. While both portions are flexible, the proximal portion is more resilient than the distal portion.

In the present example the flexible member (95) has a generally round cross-sectional geometry (solid or tubular) and is formed from a flexible resilient material (such as rubber or durometer santoprene). The dimensions of the two portions can vary, but in one embodiment, the proximal portion (95) is between about 6 and about 14 inches in length, and the distal portion (20) is between about 15 and about 20 inches in length.

Figure 6B:
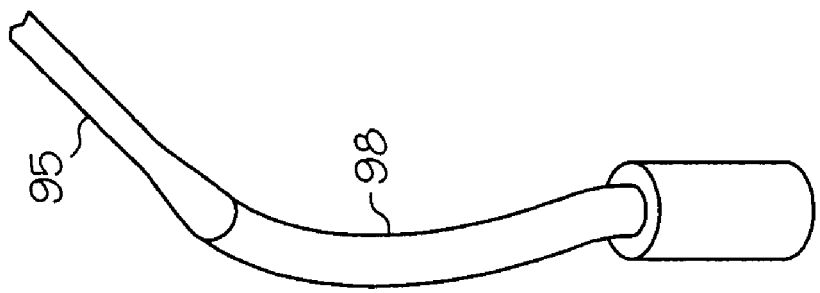
FIGS. 6a and b illustrate an instrument guide being attached to a surgical instrument.
Figure 6A:
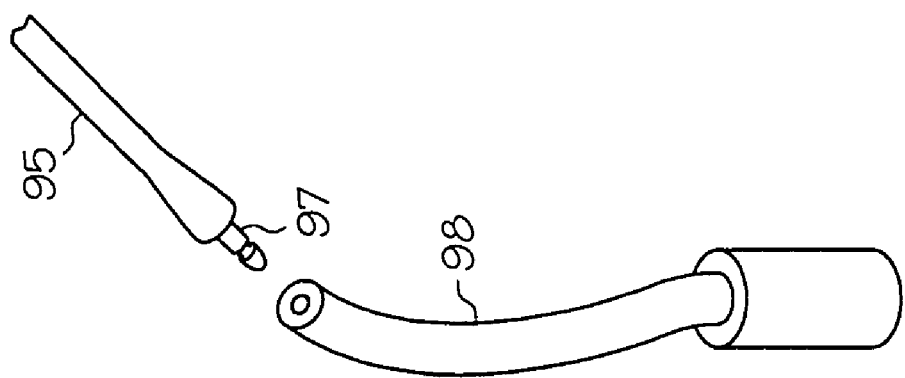

Located on or near the proximal end (94) is an anchor (97) adapted for attaching the guide (90) to a surgical instrument. As shown in FIGS. 6A&B, the anchor (97) is a male prong fastener dimensioned to engage a female fastener counterpart located on the surgical instrument (98). The guide (90) can be separated from the surgical instrument by pulling the anchor (97) in the distal direction. Preferably, a threshold pulling force is required to prevent inadvertent separation. Thus, the anchor (97) can be selectively engaged and disengaged from the surgical instrument. Alternatively, the anchor may be permanently attached to the surgical instrument. Naturally, the anchor (97) can take a variety of other forms other than the male/female arrangement described in this example, including without limitation screws or threads, snaps, adhesives, interference fits, barbs, magnets, and the like. In the present example, the surgical instrument (98) is the distal jaw of an ablation clamp; however, a variety of other surgical instruments could also be used depending on the surgical procedure and technique. As shown here, the guide (90) extends axially in-line with the jaw; however, the guide (90) could also extend at an angle from the jaw axis. Alternatively, the anchor (97) could pivotally attach to the jaw, such as with a ball and socket joint.

The following illustrates one exemplary method for using the instrument guide (90). Similar to the example illustrated in FIG. 3, a positioning mechanism is placed in the distal pocket (30). A dissection path is created between the pulmonary veins and the pericardium using the positioning mechanism. The surgeon may grasp the distal end (92) of the instrument guide (90) and pull the distal pocket (30) from the positioning mechanism. The positioning mechanism may then be backed out and removed from the surgical field. The anchor (97) is attached to the jaw (98), either before or after the dissected path is created. By continuing to pull the distal end (92) of the instrument guide (90), the distal jaw (98) may be accurately positioned in the dissected path until the pulmonary veins are interposed between the distal and proximal jaws of the ablation clamp. With the anchor (97) attached to the jaw (98), the distal and proximal jaws may then be positioned such that the tissue being treated is interposed between the jaws. The jaws may then be closed and the tissue ablated. After treatment is concluded, the distal jaw (98) is backed out of the dissection path thus pulling the instrument guide (90) behind the jaw (98) until the instrument guide (90) is removed from the surgical field.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A method for positioning a surgical instrument in a patient for treatment of a target tissue adjacent a pulmonary vein of a heart by means of an instrument guide and a positioning mechanism for the surgical instrument comprising the acts of:
   a) providing a positioning mechanism comprising a blunt distal end with a light source thereon;
   b) providing an instrument guide comprising a flexible, elongated member having a proximal end comprising an anchor, a distal end and a medial portion between the proximal and distal ends, a first translucent pocket located on the distal end of the elongated member, and a medial pocket positioned proximal to the first pocket;
   c) providing a surgical instrument comprising a surgical ablation clamp having a distal jaw and a proximal jaw, each jaw having a tip for performing a medical procedure on target tissue;
   d) placing the distal end of the positioning mechanism in the first pocket;
   e) activating the light source on the distal end of the positioning mechanism;
   f) using the distal end of the positioning mechanism to dissect tissue to create a pathway to the target tissue and to advance the first pocket to a position adjacent the target tissue;
   g) viewing the light source through the first pocket of the instrument guide to confirm the location of the distal end of the positioning mechanism relative to the target tissue;
   h) removing the positioning mechanism from the first pocket;
   i) placing one of the jaws of the surgical instrument in the medial pocket of the instrument guide, attaching the anchor to a release lever on the surgical instrument, pulling the distal end of the elongated member of the instrument guide to further advance the instrument guide until the jaws of the surgical instrument are located on the target tissue adjacent to the pulmonary vein; and
   j) ablating the target tissue with the surgical instrument.

2. The method of claim 1, wherein the acts are performed sequentially as listed.

3. The method of claim 1 wherein the first pocket comprises enclosed sides and end, and an opening opposite the end, the distal end of the positioning mechanism being introduced into the first pocket through the opening.

4. The method of claim 1 further comprising visually differentiating tissue composition with the activated light source.

5. A method for positioning a surgical instrument in a patient for treatment of a target tissue adjacent a pulmonary vein of a heart by means of an instrument guide and a positioning mechanism for the surgical instrument, the surgical instrument comprising a surgical ablation clamp having a release lever, a distal jaw and a proximal jaw, each jaw having a tip for performing a medical procedure on target tissue, the instrument guide comprising a flexible, elongated member having a proximal end comprising an anchor, a distal end and a medial portion between the proximal and distal ends, a first translucent pocket located on the distal end of the elongated member and a medial pocket positioned proximal to the first pocket, and the positioning mechanism comprising a blunt distal end with a light source thereon, the method comprising:
   a) placing the distal end of the positioning mechanism in the first pocket;

b) activating the light source on the distal end of the positioning mechanism;
c) using the distal end of the positioning mechanism to dissect tissue to create a pathway to the target tissue and to advance the first pocket to a position adjacent the target tissue;
d) viewing the light source through the first pocket of the instrument guide to confirm the location of the distal end of the positioning mechanism relative to the target tissue;
e) removing the positioning mechanism from the first pocket;
f) placing one of the jaws of the surgical instrument in the medial pocket of the instrument guide, attaching the anchor to the release lever on the surgical instrument, pulling the distal end of the elongated member of the instrument guide to further advance the instrument guide until the jaws of the surgical instrument are located on the target tissue adjacent to the pulmonary vein; and
g) ablating the target tissue with the surgical instrument.

* * * * *